US011673375B2

(12) United States Patent
Dietmann et al.

(10) Patent No.: US 11,673,375 B2
(45) Date of Patent: Jun. 13, 2023

(54) HEATER HAVING A CO-SINTERED MULTI-LAYER STRUCTURE

(71) Applicant: Heraeus Nexensos GmbH, Hanau (DE)

(72) Inventors: Stefan Dietmann, Alzenau (DE); Dieter Teusch, Bruchkoebel (DE); Tim Asmus, Allendorf-Winnen (DE); Karlheinz Wienand, Aschaffenburg (DE)

(73) Assignee: Heraeus Nexensos GmbH, Hanau (DE)

( * ) Notice: Subject to any disclaimer, the term of this patent is extended or adjusted under 35 U.S.C. 154(b) by 587 days.

(21) Appl. No.: 16/617,190

(22) PCT Filed: May 3, 2018

(86) PCT No.: PCT/EP2018/061330
§ 371 (c)(1),
(2) Date: Nov. 26, 2019

(87) PCT Pub. No.: WO2018/219584
PCT Pub. Date: Dec. 6, 2018

(65) Prior Publication Data

US 2020/0374985 A1 Nov. 26, 2020

(30) Foreign Application Priority Data

May 30, 2017 (EP) .................................... 17173559

(51) Int. Cl.
*B32B 18/00* (2006.01)
*A61M 11/04* (2006.01)
(Continued)

(52) U.S. Cl.
CPC .............. *B32B 18/00* (2013.01); *A24F 40/46* (2020.01); *A24F 40/465* (2020.01);
(Continued)

(58) Field of Classification Search
CPC .............. B32B 18/00; B32B 2305/345; B32B 2305/80; B32B 2315/02; A24F 40/46;
(Continued)

(56) References Cited

U.S. PATENT DOCUMENTS 5,059,565 A 10/1991 Peuckert et al.
5,334,350 A 8/1994 Friese et al.
(Continued)

FOREIGN PATENT DOCUMENTS

CN 101163962 4/2008
CN 103702833 4/2014
(Continued)

*Primary Examiner* — Shawntina T Fuqua
(74) *Attorney, Agent, or Firm* — Dicke, Billig & Czaja, PLLC

(57) ABSTRACT

A method for producing a heater with a co-sintered multi-layer construction for a system for providing an inhalable aerosol, including providing at least one first substrate layer, arranging at least one first insulating layer at least in areas on the first substrate layer, arranging at least one heating element at least in areas on the first insulating layer, arranging at least one second substrate layer and at least one second insulating layer at least in areas on the heating element. The second insulating layer is arranged at least in areas on the second substrate layer, and the second insulating layer is in contact at least in areas with the heating element and/or with the first insulating layer. The method includes pressing the layers and the heating element, and firing the pressed layers in order to co-sinter the layers of the multi-layer construction.

15 Claims, 2 Drawing Sheets

(51) Int. Cl.
*A24F 40/465* (2020.01)
*H05B 3/14* (2006.01)
*H05B 3/28* (2006.01)
*A24F 40/46* (2020.01)

(52) U.S. Cl.
CPC ........... *A61M 11/042* (2014.02); *H05B 3/141* (2013.01); *H05B 3/283* (2013.01); *A61M 2205/3368* (2013.01); *A61M 2207/00* (2013.01); *B32B 2305/345* (2013.01); *B32B 2305/80* (2013.01); *B32B 2315/02* (2013.01); *H05B 2203/003* (2013.01); *H05B 2203/013* (2013.01); *H05B 2203/017* (2013.01)

(58) Field of Classification Search
CPC ........ A24F 40/465; A24F 40/10; A24F 40/20; A24F 40/51; A24F 40/57; A61M 11/042; A61M 2205/3368; A61M 2207/00; H05B 3/141; H05B 3/283; H05B 2203/003; H05B 2203/013; H05B 2203/017; G01K 1/14; C04B 2235/34; C04B 2235/6567; C04B 2237/343; C04B 2237/348; C04B 2237/408; C04B 35/10; C04B 35/48; C04B 37/02; A24B 15/167; A24B 15/06
See application file for complete search history.

(56) References Cited

U.S. PATENT DOCUMENTS

| | | | | | |
|---|---|---|---|---|---|
| 5,447,618 | A * | 9/1995 | Sugiyama | G01N 27/4071 204/426 |
| 6,274,855 | B1 | 8/2001 | Tatematsu et al. | |
| 6,780,349 | B1 | 8/2004 | Lindemann et al. | |
| 7,739,908 | B2 | 6/2010 | Wienand et al. | |
| 8,183,974 | B2 | 5/2012 | Wienand et al. | |
| 8,730,002 | B2 | 5/2014 | Wiendand et al. | |
| 9,155,129 | B2 | 10/2015 | Wienand et al. | |
| 9,414,629 | B2 | 8/2016 | Egoyants et al. | |
| 10,088,405 | B2 | 10/2018 | Baars et al. | |
| 10,215,726 | B2 | 2/2019 | Bischoff et al. | |
| 2003/0126736 | A1 | 7/2003 | Watanabe et al. | |
| 2004/0094417 | A1 | 5/2004 | Noda et al. | |
| 2008/0190173 | A1* | 8/2008 | Wienand | G01N 15/0656 422/68.1 |
| 2014/0174307 | A1 | 6/2014 | Wienand et al. | |
| 2017/0110225 | A1 | 4/2017 | Loose et al. | |
| 2017/0150755 | A1* | 6/2017 | Batista | A24F 40/46 |
| 2018/0168224 | A1 | 6/2018 | Naughton et al. | |
| 2021/0033556 | A1 | 2/2021 | Muziol et al. | |
| 2021/0331433 | A1* | 10/2021 | Spalding | B29C 73/10 |

FOREIGN PATENT DOCUMENTS

| | | | |
|---|---|---|---|
| CN | 203587569 | 5/2014 | |
| CN | 106461528 | 2/2017 | |
| DE | 39 41 837 | 6/1991 | |
| DE | 4016861 | 8/1991 | |
| DE | 19545590 | 6/1997 | |
| DE | 19924134 | 11/2000 | |
| DE | 10 2005 021131 | 11/2006 | |
| DE | 10 2007 046900 | 4/2009 | |
| DE | 10 2014 104 219 | 10/2015 | |
| DE | 10 2014 211533 | 12/2015 | |
| EP | 0384342 | 8/1990 | |
| EP | 0763693 | 3/1997 | |
| EP | 1003351 | 5/2000 | |
| EP | 2 316 286 | 5/2011 | |
| JP | S60-166990 | 11/1985 | |
| JP | H08273815 | 10/1996 | |
| JP | 2000156275 | 6/2000 | |
| JP | 2004241148 | 8/2004 | |
| JP | 2006300750 | 11/2006 | |
| JP | 2013509160 | 3/2013 | |
| JP | 2017510813 | 4/2017 | |
| KR | 2012/0101637 | 9/2012 | |
| TW | 200927701 | 7/2009 | |
| WO | 2006/111386 | 10/2006 | |
| WO | 2007/048573 | 5/2007 | |
| WO | 2010/089024 | 8/2010 | |
| WO | 2011/050964 | 5/2011 | |
| WO | 2013/017185 | 2/2013 | |
| WO | 2013/034456 | 3/2013 | |
| WO | 2016/207107 | 12/2016 | |
| WO | WO-2022021236 A1 * | 2/2022 | A61M 11/00 |
| WO | WO-2022184926 A1 * | 9/2022 | |

* cited by examiner

HEATER HAVING A CO-SINTERED MULTI-LAYER STRUCTURE

CROSS REFERENCE TO RELATED APPLICATION

This Utility Patent Application claims priority under 35 U.S.C. § 371 to International Application Serial No. PCT/EP2018/061330, filed May 3, 2018, which claims the benefit of European Patent Application No. EP 17173559.0, filed May 30, 2017; both of which are incorporated herein by reference.

The present invention relates to a method for producing a heater with a co-sintered multilayer construction for a system for providing an inhalable aerosol. Furthermore, the present invention relates to the use of a heater, a system for providing an inhalable aerosol, and to a heater.

Systems with heaters for providing inhalable aerosols which heat a substance for forming the aerosol are known from the prior art. Depending on the system used, the substance can be liquid, gaseous or solid. In general, in such systems a substance comprising tobacco or a tobacco-like product is not combusted as in a conventional cigarette but only heated without the substance combusting in order to obtain an inhalable aerosol in this manner.

For example, WO 2013/034456 A1 describes the construction of a system in which tobacco or a tobacco-like product present in a storage container in the system is heated on a surface or in the vicinity of the surface of a heater until an aerosol containing nicotine and/or a flavoring substance is produced. The aerosol formed can be inhaled by a user by a mouthpiece.

Another system described by way of example for providing an inhalable aerosol is described in WO 2016/207407 A1. The system comprises a housing with an opening for introducing the substance for forming the aerosol. A heater is arranged in the housing which heats the introduced substance but does not completely combust it. The aerosol formed can also be inhaled in this example by a user by a mouthpiece.

A typical construction of a heater for a system for providing an inhalable aerosol is described in WO 2011/050964 A1 by way of example. A metallic paste is applied onto an electrically insulating substrate such as, for example, an electrically insulating ceramic material and a pattern is subsequently introduced into the applied metallic paste so that a resistance element in the form of a resistance conductor track is produced. Thereafter, the substrate with the applied metallic paste is sintered in a two-stage method. Thereafter, a passivating layer can be sintered onto the resistance conductor track in an additional step.

Even other multi-step production methods for producing more complex heaters are known from the prior art. For example, WO 2013/017185 A1 describes a heating impression stamp with a thermally insulating substrate on which an electrically conductive structure comprising a heating resistor is arranged. The electrically conductive structure is covered by an electrically insulating layer. For example, the heating impression stamp can be produced with a method in which an insulating layer is at first sintered onto an electrically conductive substrate. Subsequently, a resistance element is sintered on, onto which an insulating layer is sintered on in a further baking out step.

Therefore, the methods known from the prior art have the disadvantage that these methods require a large number of processing steps and baking out steps. As a consequence, the production of heaters for systems for providing an inhalable aerosol becomes very complex and therefore time-consuming and expensive.

Therefore, it is an object of the present invention to provide an improved method for producing a heater which overcomes the disadvantages of the prior art. In particular providing a method with which a heater can be economically and rapidly produced.

This object is achieved according to the invention by a method according to the subject matter of claim 1.

The method according to the invention for producing a heater with a co-sintered multilayer construction for providing an inhalable aerosol comprises to this end:

providing at least one first substrate layer, arranging at least one first insulating layer at least in areas on the first substrate layer, arranging at least one heating element at least in areas on the first insulating layer, arranging at least one second substrate layer and at least one second insulating layer at least in areas on the heating element, wherein the second insulating layer is arranged at least in areas on the second substrate layer, and wherein the second insulating layer is connected at least in areas to the heating element and/or to the first insulating layer, pressing the layers and the heating element, and firing the pressed layers for co-sintering the layers of the multilayer construction.

The heater can be operated for heating or evaporating a substance in a temperature range of 200° C. to 400° C. However, the heater can also be operated at least temporarily, in a higher temperature range, for example at approximately 550° C., for cleaning the heater.

The term "multilayer construction" can be used here to designate the construction comprising the different layers of the heater.

The terms "co-sintered" and "co-sintered multilayer construction" can designate a simultaneous heating and baking out of several layers of a multilayer construction, for example, under pressure or without pressure so that the layers of the multilayer construction can be fired or sintered together in a single work step. The individual layers can be pre-dried before the firing.

The steps of the method according to the invention can be carried out sequentially in an example. In another example, the steps can be carried out in any sequence and/or individual method steps can be omitted or added.

The invention is based on the surprising recognition that the number of baking out steps is reduced to a single baking out step by a co-sintering of the multilayer construction and therefore the production costs of the heater can be significantly lowered.

In an example of the invention the first substrate layer and/or the second substrate layer comprise(s) at least one green film, in particular a green film comprising stabilized zirconium oxide ZrO2.

The term "green film" can denote a substrate layer and/or a film comprising a solid component which can include organic material and inorganic material. The organic proportion of the solids can comprise, e.g., aluminum oxide, yttrium or scandium-stabilized zirconium oxide or also other ceramic, metallic or vitreous materials and in addition the inorganic component can comprise residual substances in an appropriate amount. Furthermore, the organic proportion can comprise binders, plasticizers and dispersing agents. Phthalates, polyols, glycols, phosphates and other hydrocarbons of low volatility and the like can be used as plasticizers.

A production method of a ceramic green film is described, for example, in DE 19924134 A1.

The term "stabilized zirconium oxide" can be used to designate a yttrium-stabilized zirconium dioxide as the first and/or second substrate layer such as is described, for example, in WO 2010/089024 A1. The oxygen conductivity of the first and/or second substrate layer can be suppressed by the addition of tantalum or niobium. Instead of yttrium, even other bivalent of trivalent metals such as, e.g., scandium can be used for the stabilization. A high breaking strength can advantageously be achieved by a content of 20-40 mole % stabilizer relative to the entire metal content, in particular 25-35 mole % because, as a result, the high-temperature tetragonal phase of the zirconium dioxide is retained. The mechanical strength can be further increased to more than 250 MPa by doping with HfO2.

In another example the green film has a thickness in a range between 0.25 mm and 0.5 mm.

In an example the first insulating layer and/or the second insulating layer comprise(s) an aluminum oxide, Al2O3, in particular a ceramic slip comprising aluminum oxide Al2O3.

For example, a ceramic slip comprising aluminum oxide can be used such as is described, for example, in DE4016861 A1. Here, a fine aluminum oxide powder is processed to a casting mass with the aid of other organic and inorganic additives in order to produce a green film. Such an insulating layer advantageously still has an insulating effect even at high temperatures above 1000° C. Furthermore, such an insulating layer is especially well-suited for a co-sintering on account of the excellent mechanical properties. In particular, a substantially fissure-free structure can be obtained by using such a ceramic slip.

In another example arranging the first insulating layer and/or the second insulating layer comprises:

screen-printing and/or tape casting the first insulating layer on the first substrate layer and/or the second insulating layer on the second substrate layer.

The first insulating layer and/or the second insulating layer can be arranged especially rapidly and efficiently by screen-printing and/or tape casting.

In one example the heating element comprises at least one resistance element, in particular a resistance element comprising platinum, Pt-cermet.

For example, the heating element can be constructed as a resistance element in the form of a conductor track. If a current flows through the conductor track, the heat is produced by the intrinsic resistance of the conductor track. A set heating performance of the heater can be set as a function of the current flowing through the conductor track.

The Pt-cermet is composed as follows:

45 wt. % Pt powder with a grain size of 50 μm, 45 wt. % Al2O3 powder with a grain size of 2 μm. and 10 wt. % binder, for example, METAWAX P-50 of Zschimmer & Schwarz GmbH & Co. KG, or a similar binder.

The relative proportions are each relative to the total weight of the PT-cermet.

For the production of the Pt-cermet, the Pt powder, the Al2O3 powder and the binder can be mixed on a roller block with Al2O3 balls. Then, the mixture produced can be filled into a double-Z kneader and further compounded with a dispersing agent with the addition of demineralized water, VE water, in order to remove inclusions of air.

In yet another example arranging the heating element comprises: Screen-printing of the resistance element onto the first insulating layer.

For example, the previously described mixture can be applied onto the insulating layer with at least 80% humidity by a screen-printing method.

In an example arranging the second substrate layer and the second insulating comprises:

Arranging the second insulating layer at least in areas on the heating element and arranging the second substrate layer at least in areas on the second insulating layer, or arranging the second insulating layer at least in areas on the second substrate layer and arranging the second insulating layer at least in areas on the heating element.

For example, the second insulating layer can be arranged at first on the heating element and/or on the first insulating layer so that the second insulating layer is in contact at least in areas with the heating element and/or with the first insulating layer, and thereafter the second substrate layer can be arranged on the opposite side of the second insulating layer. In another example the second insulating layer can also be arranged at first on the second substrate layer in order to then arrange the second substrate layer with the second insulating layer arranged on it together on the heating element, or to the first insulating layer in such a manner that the second insulating layer is in contact at least in areas with the heating element and/or the first insulating layer.

In another example firing the pressed layers comprises: Firing the pressed layers of the multilayer construction at at least 1400° C. for at least 36 hours.

The firing of the pressed layers can take place, for example, according to a method described in US 20040094417 A1 or in DE 19545590 C2.

In another example the method comprises:

Separating the heater before the firing, in particular by punching out or by a laser cutting method, or separating the heater after pressing the layers and before firing.

The formation of microfissures in the ceramic material can be advantageously counteracted by separating the heater prior to firing.

In an example, recesses are introduced into the second insulating layer and/or into the second substrate layer, and in particular recesses are introduced in order to expose at least in areas at least one connection means of the heating element.

These recesses serve for contacting the heating element. For example, the recesses can be designed with the shape of punched-out perforations through which at least one connection conductor can be run through for contacting connection contacts on the heating element. However, a recess can also be understood as a shortening of a respective insulating layer and/or substrate layer which makes it possible that the connection contacts are accessible from an exterior of the heater.

In another example the method comprises:

Arranging at least one temperature sensor, before the pressing of the layers, between (i) the first insulating layer and the first substrate layer, and/or (ii) the second insulating layer and the second substrate layer, and/or (iii) the first insulating layer and the second insulating layer.

The temperature of the heater can be reliably determined and accordingly the current flow through the heater can be controlled or regulated in an advantageous manner by the integral arranging of a temperature sensor between the layers.

The invention also suggests a use of a heater produced by a method according to the invention in a system for providing an inhalable aerosol.

The invention furthermore suggests a system for providing an inhalable aerosol comprising at least one heater produced by a method according to the invention.

In addition, the invention suggests a heater with a co-sintered multiple layer construction for a system for providing an inhalable aerosol, comprising:

at least one heating element with a first side and a second side opposite the first side, at least one first and one second insulating layer, wherein the first insulating layer is arranged at least in areas on the first side of the heating element, and wherein the second insulating layer is arranged at least in areas on the second side of the heating element, and at least one first substrate layer and a second substrate layer, wherein the first substrate layer is arranged at least in areas on the first insulating layer, and wherein the second substrate layer is arranged at least in areas on the second insulating layer.

Other features and advantages of the invention are apparent from the following description in which preferred embodiments of the invention are explained with reference to schematic drawings.

In the drawings:

FIG. 1 shows a schematic exploded view of a heater 1 according to an embodiment of the invention.

A first insulating layer 5 is arranged on a first substrate layer 3 which can be, in the embodiment shown, a green film, in particular a green film comprising stabilized ZrO2. In the embodiment shown, first insulating layer 5 can comprise a ceramic slip comprising Al2O3 and be arranged on first substrate layer 3 by screen-printing and/or tape casting. After arranging first insulating layer 5 on second substrate layer 3, the structure can be dried before further processing.

Figure 1:
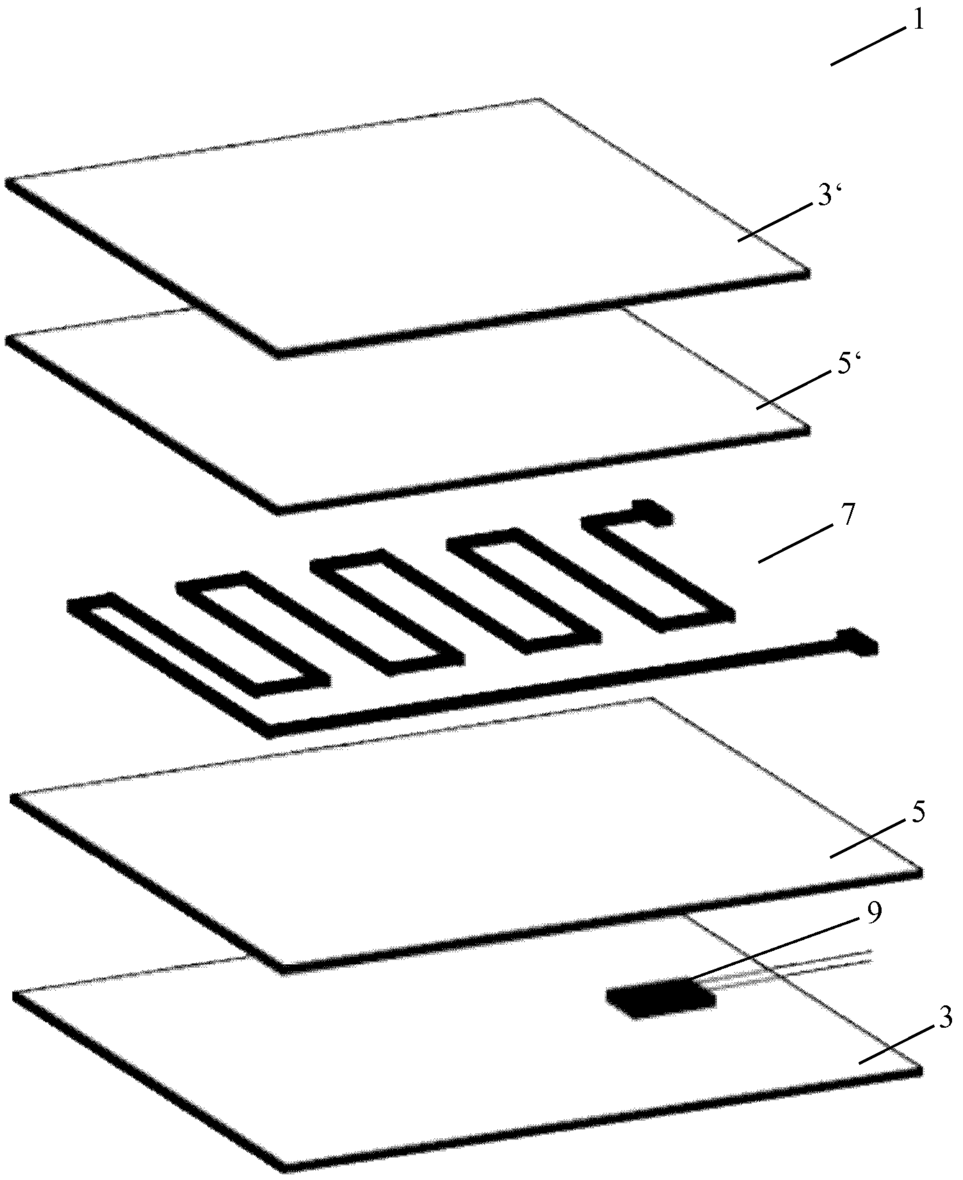
FIG. 1 shows a schematic exploded view of a heater according to an embodiment of the invention.

A temperature sensor 9 is arranged between first substrate layer 3 and first insulating layer 5 in the embodiment shown. Temperature sensor 9 serves to determine a temperature of heater 1. In FIG. 1, temperature sensor 9 is shown only optionally since such a sensor is not essential for the invention. Also, temperature 9 or several temperature sensors (not shown) can be arranged between other layers of the multilayer construction. In embodiments not shown, the temperature sensor can also be arranged between first insulating layer 5 and a second insulating layer 5' and/or between second insulating layer 5' and a second substrate layer 3'.

A heating element 7 is arranged on first insulating layer 5 in the embodiment shown. In FIG. 1, heating element 7 is designed as a resistance element in the form of a conductor track. In the embodiment shown, the resistance element can comprise a Pt-cermet and be arranged by a screen-printing method on first insulating layer 5. In FIG. 1 the resistance element is shown as a conductor track run in a meandering manner and with two connection contacts. In embodiments not shown, the conductor track can also have a different design. For example, the conductor track can also be designed in a helical form. The heating element can also assume the function of a temperature sensor by a suitable electronic control in an embodiment not shown.

In the embodiment shown, second insulating layer 5' is arranged on heating element 7 and is again arranged on second substrate layer 3'. The materials of first and second insulating layers 5, 5' and of first and second substrate layers 3, 3' can be substantially identical. Also, second insulating layer 5' and second substrate layer 3' can be arranged successively in a similar manner to that of first insulating layer 5 and of first substrate layer 3. As an alternative to the above, second insulating layer 5' can also be arranged at first on second substrate layer 3' in order to then arrange second substrate layer 3' with second insulating layer 5' arranged on it together on heating element 7.

In the embodiment shown, recesses in the form of a shortening of second insulating layer 5' relative to first insulating layer 5 and of second substrate layer 3' relative to first substrate layer 3 are introduced into second insulating layer 5' and into second substrate layer 3' in order to expose the connection contacts of heating element 1 at least in areas. In embodiments not shown, the recesses can also be designed in the form of punched-out perforations through which the respective at least one connection conductor can be run through in order to contact the heating element 7.

The layers of the multilayer construction shown in FIG. 1 are substantially planar or level. However, in embodiments not shown, these layers can also exhibit a concave or convex curvature or be bent in the form of a cylinder in order to surround the substance to be heated. For example, in this embodiment not shown, the substance to be heated can be arranged in the cylinder or pushed into it.

Figure 2:
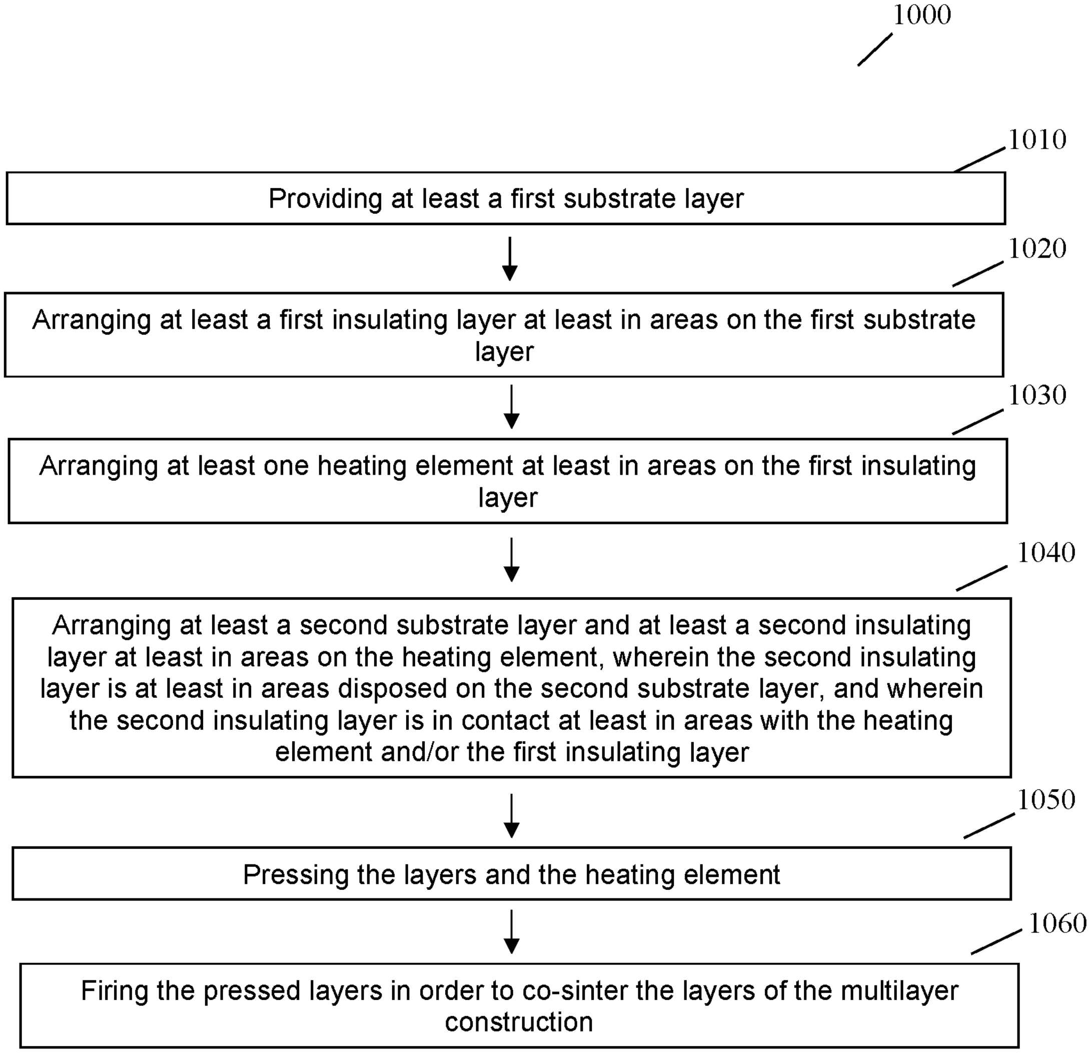
FIG. 2 shows a method for producing a heater according to an embodiment of the invention.

FIG. 2 shows a method for producing a heater according to an embodiment of the invention.

The method shown for producing a heater with a co-sintered multilayer construction for a system for providing an inhalable aerosol comprises the following steps:

providing 1010 at least one first substrate layer, arranging 1020 at least one first insulating layer at least in areas on the first substrate layer, arranging 1030 at least one heating element at least in areas on the first insulating layer, arranging 1040 at least one second substrate layer and at least one second insulating layer at least in areas on the heating element, wherein the second insulating layer is arranged at least in areas on the second substrate layer, and wherein the second insulating layer is in contact at least in areas with the heating element and/or the first insulating layer, pressing 1050 the layers and the heating element, and firing 1060 the pressed layers for the co-sintering of the layers of the multilayer construction.

The features presented in the description above, in the claims and in the figures can be essential for the invention in its different embodiments individually as well as in any combination.

LIST OF REFERENCE NUMERALS

1 Heater
3,3' Substrate layer
5, 5' Insulating layer
7 Heating element
9 Temperature sensor
1010 Providing the first substrate layer
1020 Arranging the first insulating layer
1030 Arranging the heating element
1040 Arranging the second substrate layer and the second insulating layer
1050 Pressing
1060 Firing

The invention claimed is:

1. A method for producing a heater with a co-sintered multilayer construction for a system for providing an inhalable aerosol, the method comprising:
providing at least one first substrate layer;
arranging at least one first insulating layer at least in areas on the first substrate layer;
arranging at least one heating element at least in areas on the first insulating layer, arranging at least one second substrate layer and at least one second insulating layer at least in areas on the at least one heating element, wherein the at least one second insulating layer is arranged at least in areas on the at least one second substrate layer, and wherein the at least one second insulating layer is in contact at least in areas with the at least one heating element and/or with the at least one first insulating layer;
pressing the layers and the heating element; and
firing the pressed layers in order to co-sinter the layers of the multilayer construction.

2. The method according to claim 1, wherein the at least one first substrate layer and/or the at least one second substrate layer comprise(s) at least one green film comprising stabilized zirconium oxide, $ZrO_2$.

3. The method according to claim 2, wherein the at least one green film has a thickness in a range between 0.25 mm and 0.5 mm.

4. The method according to claim 1, wherein the at least one first insulating layer and/or the at least one second insulating layer comprises a ceramic slip comprising aluminum oxide, $Al_2O_3$.

5. The method according to claim 1, wherein arranging the at least one first insulating layer and/or of the at least one second insulating layer comprises: screen-printing and/or tape casting the at least one first insulating layer on the at least one first substrate layer and/or the at least one second insulating layer on the at least one second substrate layer.

6. The method according to claim 1, wherein the at least one heating element comprises at least one resistance element comprising platinum, Pt-cermet.

7. The method according to claim 6, wherein arranging the at least one heating element comprises screen-printing of the at least one resistance element on the at least one first insulating layer.

8. The method according to claim 1, wherein arranging the at least one second substrate layer and the at least one second insulating layer comprises:
arranging the at least one second insulating layer at least in areas on the at least one heating element and arranging the at least one second substrate layer at least in areas on the at least one second insulating layer, or
arranging the at least one second insulating layer at least in areas on the at least one second substrate layer and arranging the at least one second insulating layer at least in areas on the at least one heating element.

9. The method according to claim 1, wherein firing of the pressed layers comprises:
firing the pressed layers of the multilayer construction at a temperature of at least 1400° C. for at least 36 hours.

10. The method according to claim 1, comprising separating the heater before firing by punching out or by a laser cutting method, or separating the heater after pressing the layers and before firing.

11. The method according to claim 1, comprising introducing recesses into the at least one second insulating layer and/or into the at least one second substrate layer, by introducing recesses for exposing at least one connection means of the at least one heating element at least in areas.

12. The method according to claim 1, comprising:
arranging at least one temperature sensor before the pressing of the layers between:
(i) the at least one first insulating layer and the at least one first substrate layer, and/or
(ii) the at least one second insulating layer and the at least one second substrate layer, and/or
(iii) the at least one first insulating layer and the at least one second insulating layer.

13. Use of a heater produced by a method according to claim 1 in a system for providing an inhalable aerosol.

14. A system for providing an inhalable aerosol, comprising at least one heater produced by a method according to claim 1.

15. A heater with a co-sintered multiple layer construction for a system for providing an inhalable aerosol, comprising:
at least one heating element with a first side and a second side opposite the first side,
at least one first and one second insulating layer, wherein the first insulating layer is arranged at least in areas on the first side of the heating element such that there is no space between the first insulating layer and the heating element, and wherein the second insulating layer is arranged at least in areas on the second side of the heating element such that there is no space between the second insulating layer and the heating element, and
at least one first substrate layer and a second substrate layer, wherein the first substrate layer is arranged at least in areas on the first insulating layer, and wherein the second substrate layer is arranged at least in areas on the second insulating layer; and
at least one temperature sensor arranged between:
(i) the at least one first insulating layer and the at least one first substrate layer, or
(ii) the at least one second insulating layer and the at least one second substrate layer, or
(iii) the at least one first insulating layer and the at least one second insulating layer.

* * * * *